(12) United States Patent  
Lu (10) Patent No.: US 7,851,211 B2
(45) Date of Patent: *Dec. 14, 2010

(54) ALGA MICROBE PHOTOSYNTHETIC REACTION SYSTEM

(76) Inventor: Chao-Hui Lu, 7F., No. 1029, Ta Hsueh Rd., Hsin Chu City (TW)

( * ) Notice: Subject to any disclaimer, the term of this patent is extended or adjusted under 35 U.S.C. 154(b) by 914 days.

This patent is subject to a terminal disclaimer.

(21) Appl. No.: 11/714,830

(22) Filed: Mar. 7, 2007

(65) Prior Publication Data

US 2008/0220514 A1 Sep. 11, 2008

(51) Int. Cl.
  *C12M 1/00* (2006.01)
  *C12M 3/00* (2006.01)
  *B01D 35/18* (2006.01)
  *C02F 1/02* (2006.01)

(52) U.S. Cl. ............... 435/292.1; 435/286.6; 435/293.1; 435/293.2; 435/304.1; 96/155; 96/204; 55/385.4; 210/180; 210/181; 210/188

(58) Field of Classification Search ............... 435/292.1, 435/286.6, 293.1, 293.2, 304.1; 96/155, 96/204; 55/385.4; 210/180, 181, 188

See application file for complete search history.

(56) References Cited

U.S. PATENT DOCUMENTS

| | | | | |
|---|---|---|---|---|
| 3,778,973 A | * | 12/1973 | Martinez | ............... 96/155 |
| 4,868,123 A | * | 9/1989 | Berson et al. | ............... 435/286.6 |
| 5,674,199 A | * | 10/1997 | Brugger | ............... 604/122 |
| 6,083,740 A | * | 7/2000 | Kodo et al. | ............... 435/266 |
| 7,141,099 B2 | * | 11/2006 | Ross et al. | ............... 96/155 |
| 2005/0260553 A1 | * | 11/2005 | Berzin | ............... 435/3 |
| 2009/0137031 A1 | * | 5/2009 | Hirabayashi | ............... 435/292.1 |

FOREIGN PATENT DOCUMENTS

CN 95219504.6 9/1996

OTHER PUBLICATIONS

English translation of CN 95219504.6, Sep. 4, 1996, C. Miao.*

* cited by examiner

*Primary Examiner*—Nathan A Bowers
(74) *Attorney, Agent, or Firm*—Rosenberg, Klein & Lee (57) ABSTRACT

An alga microbe photosynthetic reaction system is used to circularly cultivate alga microbes and a culture medium infused in the system. The system comprises a photosynthetic reaction unit, a communicating unit, a pressure liquid infusion unit, an injection and oxygen discharging device, and a regulation area. The photosynthetic reaction unit is a light permeable pipeline. The injection and oxygen discharging device is assembled with an oxygen discharge can and a liquid collection can. By the connection and the functioning of the photosynthetic reaction unit, the communicating unit, the pressure liquid infusion unit, the injection and oxygen discharging device, and the regulation area, the alga microbe culture solution can circularly cultivate good quality algae in the system. The system further comprises a heating unit, a watering unit, and a light complement unit to control the ambient temperature and the light source to suit all kinds of algae.

12 Claims, 6 Drawing Sheets

ALGA MICROBE PHOTOSYNTHETIC REACTION SYSTEM

BACKGROUND OF THE INVENTION

1. Field of the Invention

This invention relates to a photosynthetic reaction system and method for the same and particularly relates to an alga microbe photosynthetic reaction system and method for the same that is used to cultivate alga microbes.

2. Description of Related Art

Spirulina, a blue-green alga, is high in protein, minerals, vitamins, and fermenting organisms that are beneficial to human health. It is widely recommended as a part of a healthy diet. Through a photosynthetic reaction system, a cultivation liquid for spirulina can be added into the growing environment so that enough photosynthesis occurs to supply ample nutrients to the cells of the algae. Oxygen can then be evaporated from the cultivation liquid so that the spirulina may grow and multiply in large quantities.

A conventional photosynthetic reaction system for spirulina uses a large, open-air cultivation pond. The cultivation liquid for spirulina is contained in the cultivation pond to assist in achieving photosynthesis. However, the cultivation pond requires a large area, consumes lots of energy, and the photosynthetic reaction is often affected by the weather. Pollution also affects the outcome, decreasing the algae's quality. As such, the prior art method for producing the spirulina has many drawbacks for producers.

Another conventional photosynthetic reaction system for the spirulina is a photosynthetic reaction apparatus for spirulina described in Chinese Patent No. CN95219504.6. The apparatus is formed with a reaction tower and a vertical flat spiral piping of double rows. The reaction tower and piping are made of a material that is light permeable thus allowing photosynthesis to occur. A bulla plate and a cooling and heating exchanger are provided in the reaction tower to extract oxygen from the cultivation liquid and to control the temperature of the cultivation liquid. The photosynthetic reaction apparatus for spirulina exists mainly to provide a sealed recycling system as a solution to various problems occurring in conventional cultivation ponds. Industrialized mass production of the photosynthetic reaction for spirulina is not recommended because the reactor faces many problems, such as difficulties in extracting the oxygen, controlling the temperature of the cultivation liquid, and maintaining the cleanliness of the reaction tower so as to reduce the effect of photosynthetic and impact the quality of algae.

For this reason, in consideration of improving upon the defects described above, the inventor, having concentrated their studies and operating in coordination with academic theories, has finally provided this invention as a reasonable design and an effective improvement over the defects mentioned above.

SUMMARY OF THE INVENTION

This invention provides an alga microbe photosynthetic reaction system, occupying less area, consuming less power, constantly working irrespective of the weather, and preventing the alga from becoming polluted, thereby ensuring its quality. Furthermore, the present invention discharges oxygen out of the alga and precisely controls the temperature, light intensity and source of the cultivation liquid in order to make the alga grow and multiply quickly and in large quantities thereby reducing the costs of the manufacturer.

In order to achieve the object, this invention provides an alga microbe photosynthetic reaction system comprising a photosynthetic reaction unit, a connected unit, a pressure liquid infusion unit, an injection and oxygen discharging device, and a regulation area. The photosynthetic reaction unit is a light permeable pipeline, and the connected unit leads to an outlet of the light permeable pipeline and an inlet of the pressure liquid infusion unit. The injection and oxygen discharge device is a hollow pipe, comprising an oxygen discharge can and a liquid collection can that are connected together. The oxygen discharge can is provided with a liquid entrance, a top exhaust, and a hollow pipe wall, in which the liquid entrance leads to an exit of the pressure liquid infusion unit. The top exhaust is located at a top of the oxygen discharge can. The hollow pipe wall extends from the top exhaust downwards, while the regulation area leads to the liquid collection can and the entrance of the light permeable pipeline, respectively.

Regarding the advantages of this invention, through connections between the photosynthetic reaction pipeline, the connected unit, the pressure liquid infusion module, the oxygen injection and discharge device, and the regulation area, the algae microbe cultivation liquid and algae seeds infused herein may circularly cultivate the algae microbe within multiple rows of straight sealed piping; thus, such an arrangement allows the system to occupy less area and consume less power. The alga can be cultivated in an airtight space, so the system works irrespective of the weather and prevents the alga from becoming polluted, thereby ensuring its quality.

Next, through the arrangement of the liquid entrance, the top exhaust, and the hollow pipe wall, any oxygen that forms in the cultivation liquid is quickly evaporated, thus maximizing production efficiency.

Further, a sprinkling device is provided outside the alga microbe photosynthetic reaction system according to this invention and a heating unit is provided between the light permeable pipeline and the pressure liquid infusion unit; thus, the temperature is regulated to keep the temperature of the cultivation liquid in a proper range for alga cultivation. A light complement unit is also provided on one or two sides of the light permeable pipeline to adjust the light intensity or source. Also, a valve is provided in the leading pipeline between the liquid collection can and the regulation area to discharge the cultivation liquid for washing, and may serve as an extraction port.

In order to further know the features and technical means of this invention, refer to the detailed description according to this invention accompanied with drawings; however, the accompanied drawings are provided for reference and illustration only and are not limited to this invention.

DETAILED DESCRIPTION OF THE PREFERRED EMBODIMENTS

Now, the present invention will be described more specifically with reference to the following embodiments. It is to be noted that the following descriptions of preferred embodiments of this invention are presented herein for purpose of illustration and description only; it is not intended to be exhaustive or to limit the present invention to the precise form disclosed.

Figure 1:
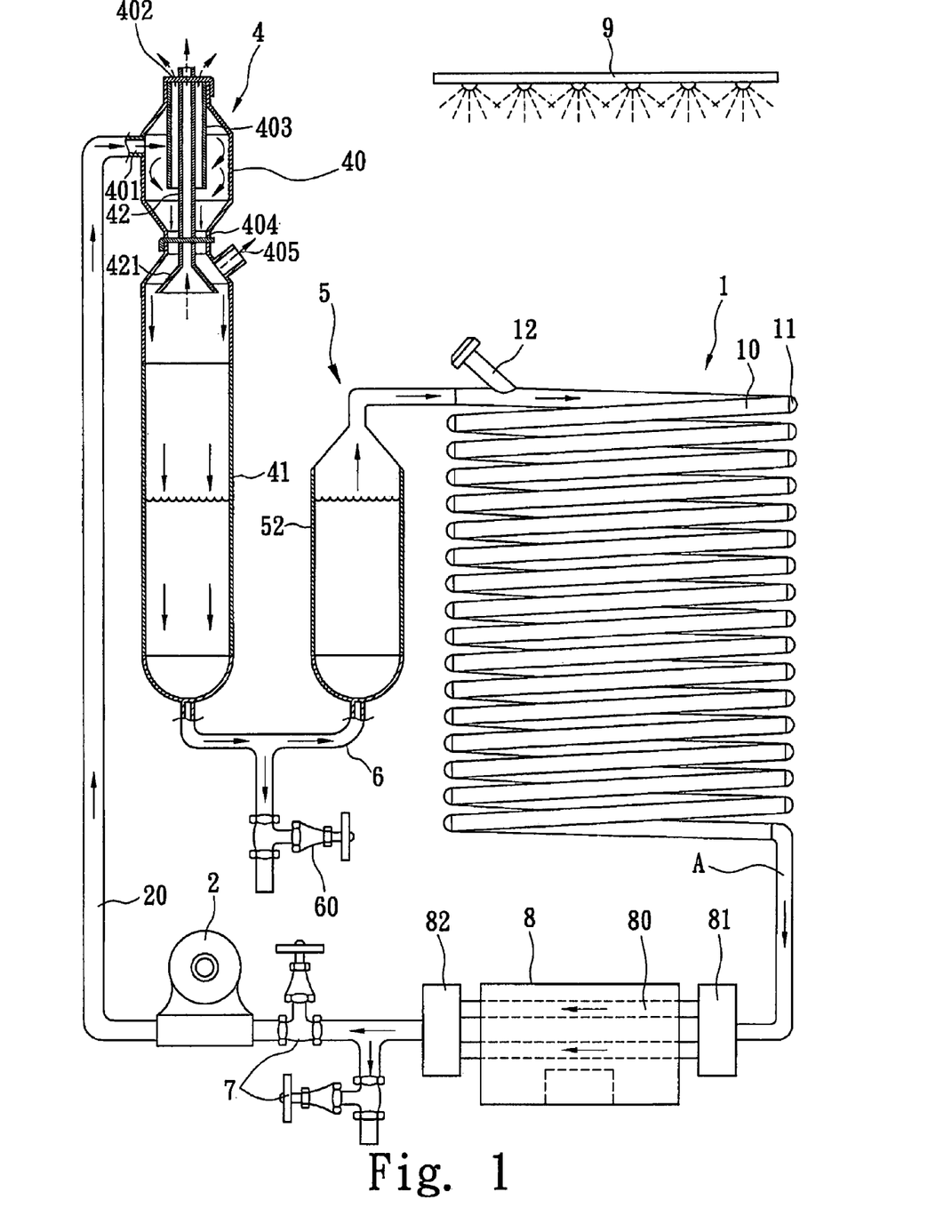
FIG. 1 is a schematic view illustrating a first embodiment of this invention.
Figure 2:
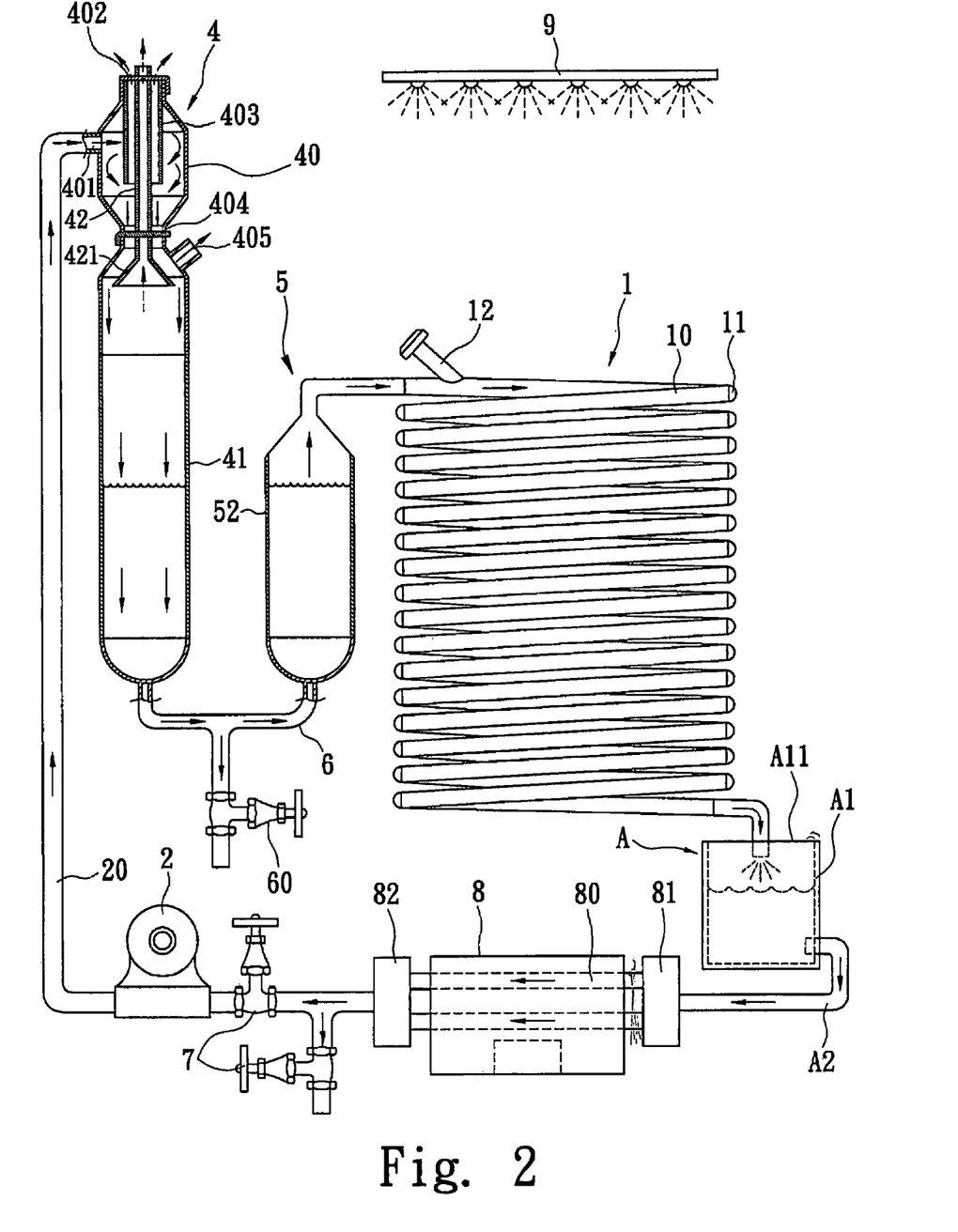
FIG. 2 is a schematic view illustrating a second embodiment of this invention.

Referring to FIGS. 1 and 2, this invention relates to an alga microbe photosynthetic reaction system used to cultivate alga microbe, such as spirulina. The alga microbe photosynthetic reaction system comprises a photosynthetic reaction unit 1, a communicating unit A, a pressure liquid infusion unit 2, an injection and oxygen discharging device 4, a regulation area 5, and a communicating device 6.

The photosynthetic reaction unit 1 is a light permeable pipeline made of a light permeable material such as glass, comprising a plurality of straight pipes 10 and a plurality of bent pipes 11. The straight pipes 10 and the bent pipes 11 are serially connected at intervals to form a spiral light permeable pipeline of double inclined rows. An auxiliary mouth 12 is provided at a topmost section of the light permeable pipeline.

The communicating unit A is connected to the exit of the light permeable pipeline, and serves as a connecting tube to lead to the exit of the light permeable pipeline and the entrance of the pressure liquid infusion unit 2, allowing cultivation liquid to flow directly towards the pressure liquid infusion unit 2. Alternatively, referring to FIG. 2, the communicating unit A can also serve as a liquid collection tank A1 having an opening A11, and a flow tube A2. The shape of the liquid collection tank A1 is not limited, and the tank A1 may be made of a light-permeable material or a non-light-permeable material and leads to the outlet of the light permeable pipeline to collect the cultivation liquid. The flow tube A2 is connected to the inlet of the liquid collection tank A1 and the pressure liquid infusion unit 2, thereby allowing the collected cultivation liquid to flow towards the pressure liquid infusion unit 2. A light-permeable material may be used to cover the opening A11 of the liquid collection tank A1 to keep dust in air from entering therein, or the liquid collection tank A1 may be placed in a cleanroom to isolate the liquid from dust in air. The pressure liquid infusion unit 2 is a pressure liquid infusion pump in which an entrance is connected to an outlet of the communicating unit A.

The injection and oxygen discharge device 4 is a hollow pipe, comprising an oxygen discharge can 40 and a liquid collection can 41. The oxygen discharge can 40 may be made of a stainless steel material, while the liquid collection can 41 may be made of a light permeable material of glass, acryl or a non-light-permeable material, such as a stainless steel material. An upper segment of the oxygen discharge can 40 is provided with a liquid entrance 401, a top exhaust 402, and a hollow pipe wall 403. The liquid entrance 401 and an infusion pipe 20 lead to an exit of the pressure liquid infusion unit 2. The top exhaust 402 is located at a top of the oxygen discharge can 40. The hollow pipe wall 403 extends from the top exhaust 402 downwards and is correspondingly located at an inside of the liquid entrance 401.

A middle section of the oxygen discharge can 40 is provided with a necking portion 404 and a side exhaust 405, in which the side exhaust 405 is located below the necking portion 404. The n injection and oxygen discharge device 4 further comprises an exhaust pipe 42 disposed inside the oxygen discharge can 40, in which a top end of the exhaust pipe 42 pierces through the hollow pipe wall 403, and a bottom end of the exhaust pipe 42 is further formed with a expansion portion 421 and is correspondingly located at an inner side of the side exhaust 405. The shape of the expansion portion 421 may vary with the requirements of different types of algae seeds, or it is possible that the expansion portion 421 is not formed depending on real requirements.

The regulation area 5 is provided with an expansion pipe 52, one end of which leads to the photosynthetic reaction unit 1 while the other end leads to the liquid collection can 41 of the injection and oxygen discharge device 4 through the communicating device 6 connected to a bottom of the liquid collection can 41 and a bottom of the regulation can 5. The communicating device 6 also has a switch valve component 60. The entrance of the light permeable pipeline is bent downwards to lead to the regulation area 5.

The alga microbe photosynthetic reaction system according to this invention further comprises a harvesting valve component 7. The harvesting valve component 7 is connected between the outlet of the communicating unit A and the inlet of the pressure liquid infusion unit 2 so as to extract out the alga microbes and cultivation liquid flowing in the light permeable pipeline.

When the alga microbe photosynthetic reaction system according to this invention is used, the alga microbe seeds and the cultivation liquid for alga microbe are infused through the auxiliary mouth 12 to the light permeable pipeline to generate photosynthesis and oxygen. The cultivation liquid flows towards the communicating unit A and then the pressure liquid infusion unit 2. The pressure liquid infusion unit 2 forces the cultivation liquid to flow from the light permeable pipeline to the injection and oxygen discharge device 4. When the cultivation liquid is injected into the liquid entrance 401 and then into the oxygen discharge can 40, the cultivation liquid first is forced into the oxygen discharge can 40 of the injection and oxygen discharge device 4 and releases a spray of water thereby discharging oxygen out of the top exhaust 402. After falling into the necking portion 404 to be collected, the cultivation liquid is forced into the expansion portion 421 and forms a spray of water thereby discharging oxygen out of the side exhaust 405. Finally, the cultivation liquid falls into the liquid collection can 41 and is collected so that the oxygen is discharged out of the exhaust pipe 42. Thus, most of the oxygen is discharged in a way that improves the performance of the process. The oxygen discharge can 40 may be made of a stainless steel material because the cultivation liquid passing through the oxygen discharge can 40 produces a saturated liquid containing oxygen that does not easily conduct photosynthesis. Furthermore, when the cultivation liquid is collected in the liquid collection can 41, most of the oxygen has already been discharged and photosynthesis may occur. As such, the liquid collection can 41 should be made of a light permeable material such as glass or of a non-light-permeable material, such as a stainless steel material, that does not allow photosynthesis to take place.

When the cultivation liquid flows through the communicating device 6 to the regulation area 5, the switch valve component 60 can be temporarily enabled to cleanse thicker sediments from the liquid. The cultivation liquid may also be sampled for testing and the component 60 may serve as a port for extraction. By a level of the cultivation liquid collected in the liquid collection can 41 that is higher than a topmost section of the light permeable pipeline of the photosynthetic reaction unit 1 and by a difference of potential energy and a gravitational effect, the cultivation liquid is made to flow towards the light permeable pipeline by itself from the regulation area 5 and further to flow towards the pressure liquid infusion unit 2. Thus, the cultivation liquid may circularly cultivate the alga microbes to gradually multiply in the alga microbe photosynthetic reaction system according to this invention. After the expected quantity of alga microbes in the cultivation liquid is ready for harvesting, harvesting valve component 7 may be enabled to harvest the alga microbes and a switch valve component 60 may also be enabled for high speedy harvesting. In the course of cultivation, the cultivation liquid flows through the communicating device 6 to the regulation area 5. The regulation area 5 is provided with an expansion pipe 52, so the cultivation liquid flows increasingly slow, thereby the cultivation liquid spends much more time flowing through the expansion pipe 52 to the light permeable pipeline. Thus, the alga microbes in the cultivation liquid have enough time for physiological conditioning in the regulation area so as to prevent harm caused by the working pressure liquid infusion unit 2 and the oxygen injection and discharge device 4, and flow to the light permeable pipeline in the best physiological status; consequently, high-quality alga may be harvested.

Figure 5:
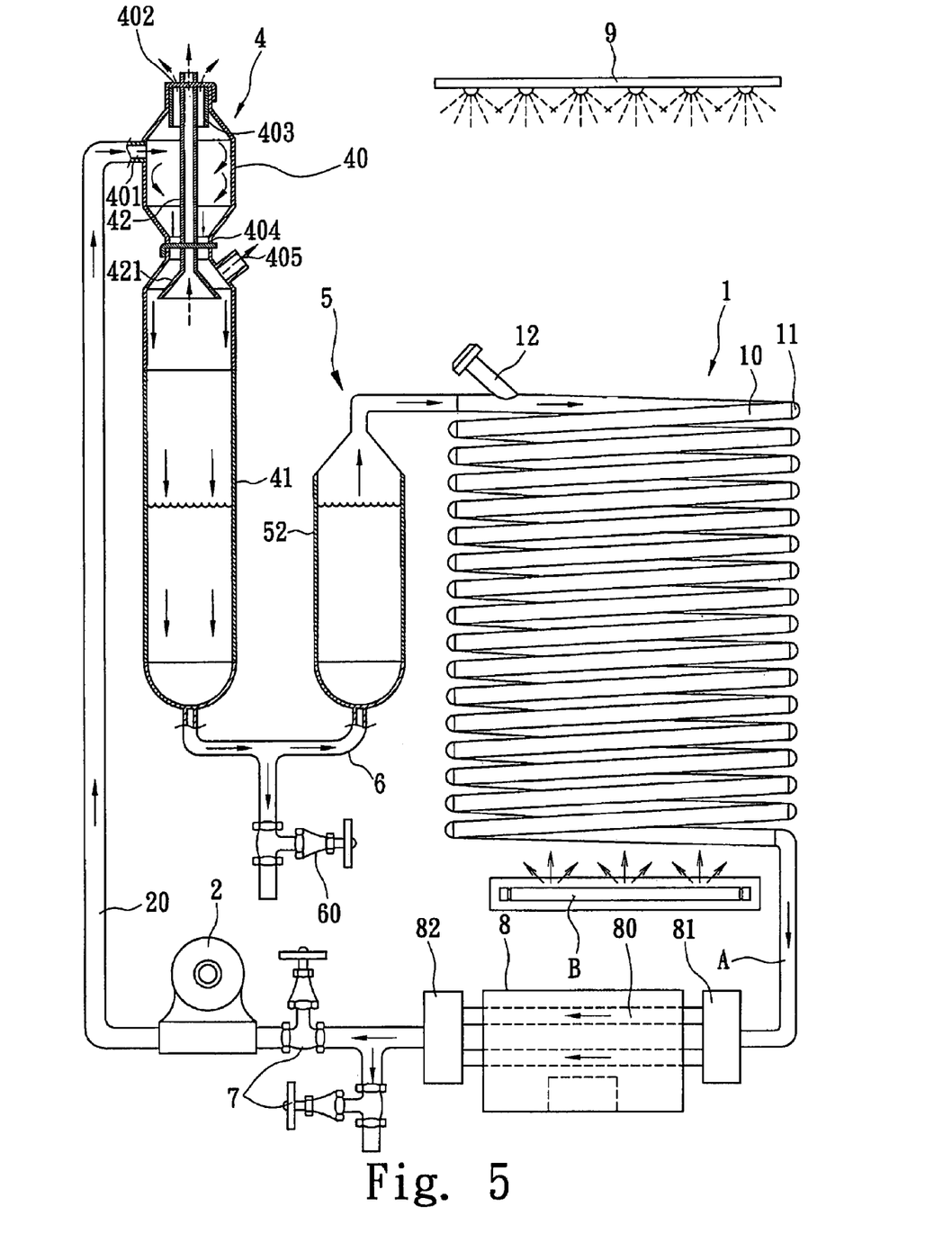
FIG. 5 is a schematic view illustrating a fifth embodiment of this invention.

Further, the alga microbe photosynthetic reaction system according to this invention comprises a heating unit 8, a sprinkling unit 9, and at least one light complement unit B (as shown in FIG. 5).

The heating unit 8 may be provided with a plurality of heating/cooling tubes 80, an entrance forwarding section 81, and an exit forwarding section 82. The heating/cooling tubes 80 may be respectively connected through the entrance forwarding section 81 and the exit forwarding section 82 between the outlet of the communicating unit A and the inlet of the pressure liquid infusion unit 2. The heating unit 8 can be controlled manually or through an automatic sensor and heats water therein. The heated water delivers heat to the heating pipes 80 to control the temperature of the cultivation liquid or the cold, water may be poured into the heating unit 8 to lower the temperature of cultivation liquid. Alternatively, the heating unit 8 can be controlled manually or through an automatic sensor and cool water therein to lower the temperature of cultivation liquid.

The sprinkling unit 9 is located above the photosynthetic reaction unit 1. It can be operated either manually or through an automatic sensor at either a predetermined time or when the environment reaches a predetermined temperature. According to the requirements of the environment, it can lower the temperature of the cultivation liquid in the light permeable pipeline.

With reference to FIG. 5, the light complement unit B may be a fluorescent lamp or another source, such as LEDs, and the amount of the unit B is determined depending on physical requirements and may be arranged at a random side of the light-permeable pipeline, such as above or below the light-permeable pipeline. In a figure of this invention, the downside of the light-permeable pipeline is implemented as an embodiment, and the light source of the light complement unit B may be either a white light, a red light, or a blue light, through which the light intensity or source may be adequately adjusted for the light-permeable pipeline so that the light intensity or source may further be changed depending on environments for different alga to grow, thereby the yield is increased and costs are decreased.

Figure 3:
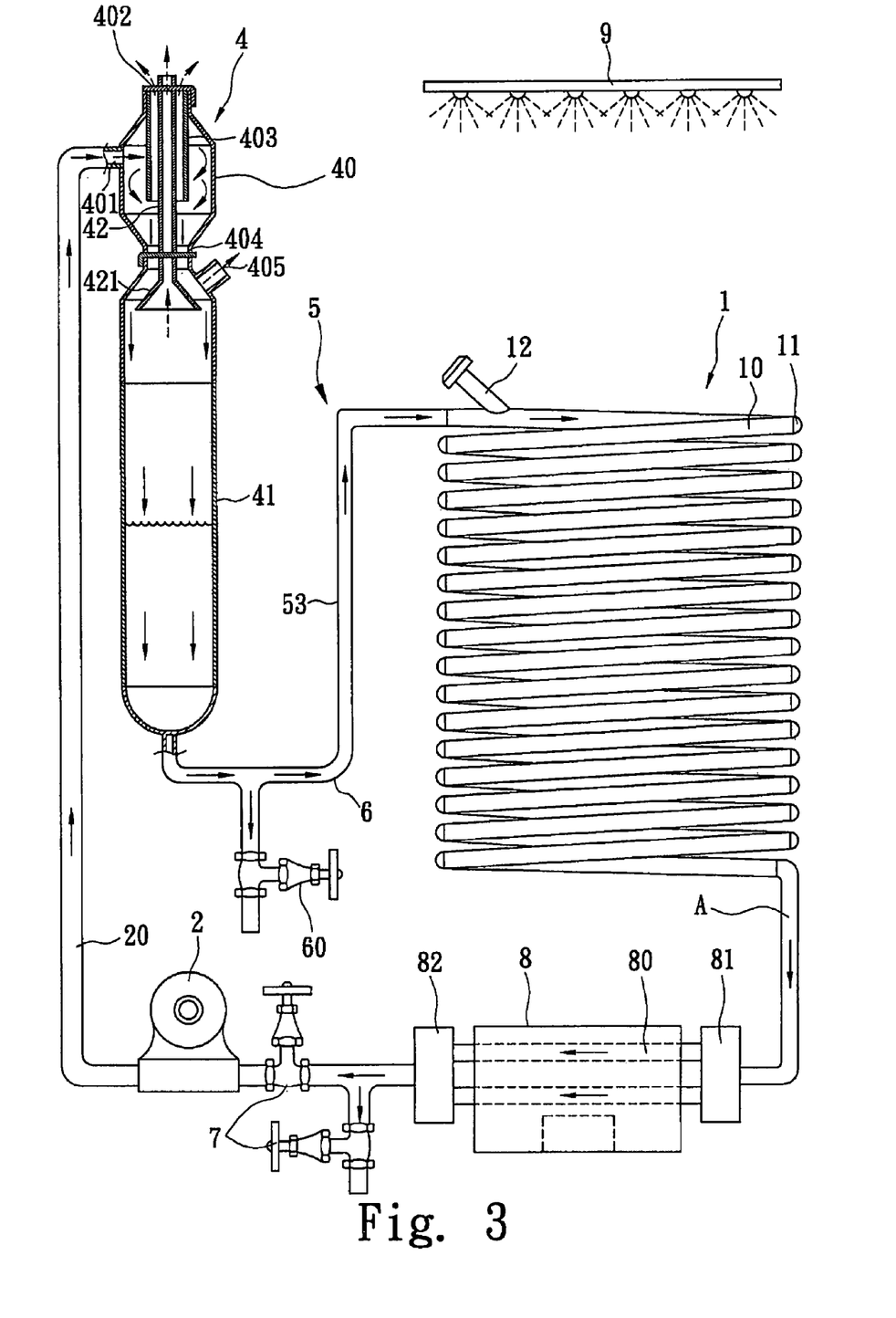
FIG. 3 is a schematic view illustrating a third embodiment of this invention.

Next, with reference to FIG. 3, in the embodiment of this invention, a straight pipe 53 is provided at the regulation area 5 of the alga microbe photosynthetic reaction system. One end of the regulation area 5 also leads to the photosynthetic reaction unit 1, while the other end of the regulation area 5 leads likewise to the liquid collection can 41 through the communicating device 6. The alga microbes likewise flow through the regulation area 5 provided with the straight pipe 53 to the photosynthetic reaction unit 1 for circular cultivation. The regulation area 5 is provided mainly for the physiological conditioning of alga microbe, so the regulation area 5 provided with the straight pipe 53 is used for the alga microbes that require less time for physiological conditioning so that the alga microbes may quickly flow to the light permeable pipeline for circular cultivation, while the regulation area 5 provided with the expansion pipe 52 as shown in FIG. 1 must be used for the alga microbes that require more time for physiological conditioning, decelerating the flow of cultivation liquid for the alga microbes in the regulation area 5 and then giving the alga microbes enough time for physiological conditioning.

Figure 4:
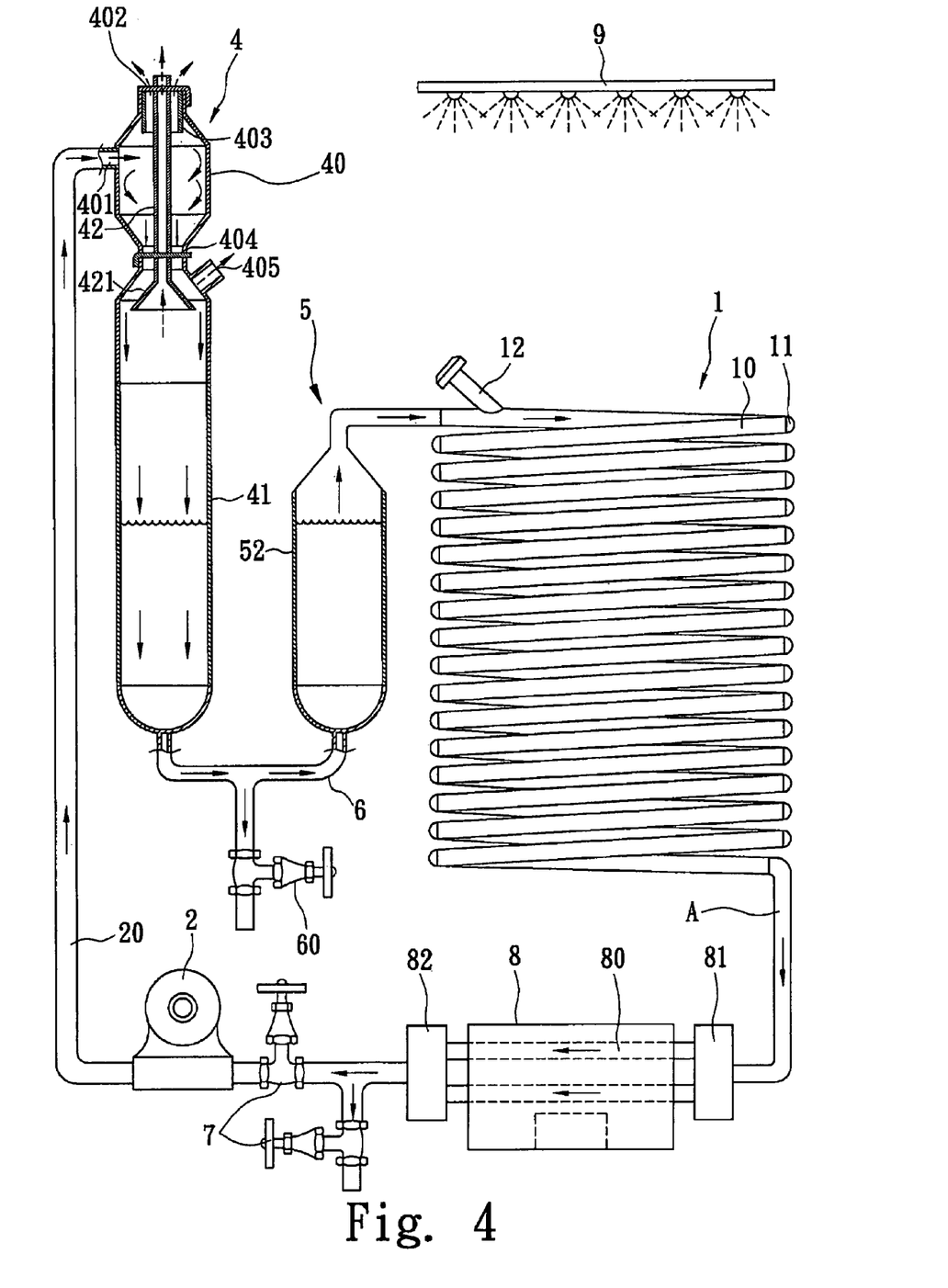
FIG. 4 is a schematic view illustrating a fourth embodiment of this invention.

With reference to FIG. 4, in this embodiment, improvement is made to the situation of generating more oxygen. When the quantity of generated oxygen increases, the quantity of oxygen to be discharged must increase. Thus, in this embodiment, the hollow pipe wall 403 is reduced in length corresponding to the top of liquid entrance 401 and is positioned relatively higher than the liquid entrance 401. When the cultivation liquid is injected into the oxygen discharge can 40 through the oxygen injection and discharge device 4 and forced into the exhaust pipe 42, part of the oxygen may be discharged without waiting for a spray of impacted water sprayed round and round, thereby the quantity of discharged oxygen increases greatly. However, the quantity of the cultivation liquid may slightly decrease, because part of the liquid splashes out of the top exhaust 402, when the cultivation liquid is forced into the exhaust pipe 402.

Figure 6:
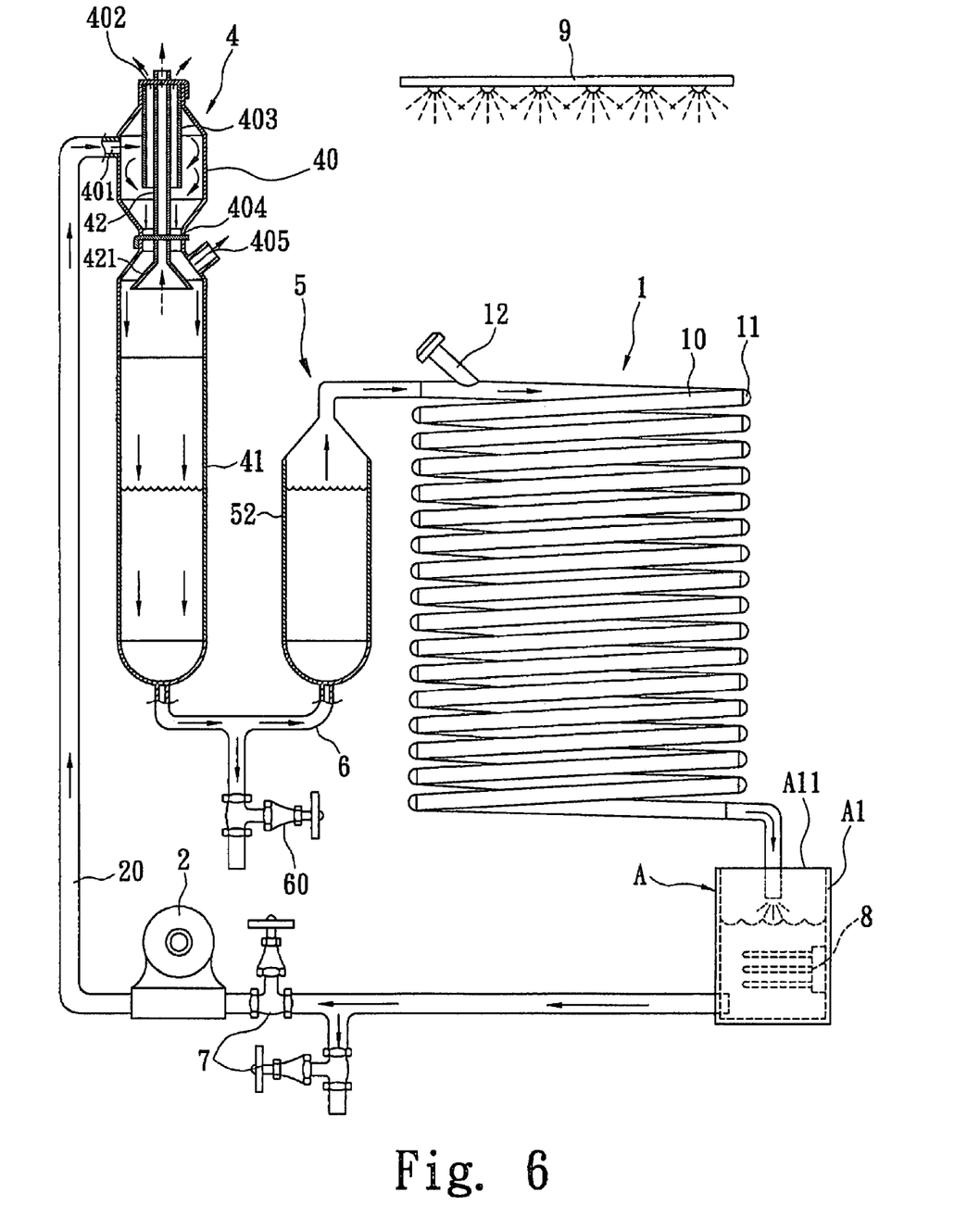
FIG. 6 is a schematic view illustrating a sixth embodiment of this invention.

With reference to FIG. 6, in this embodiment, modifications to different positions of the heating unit 8 are described. When the communicating unit A is in the form of the liquid collection tank A1, the heating unit 8 may be positioned at the liquid collection tank A1. Depending on physical requirements, the heating unit 8 may be arranged in the liquid collection tank A1 or at another appropriate site of the liquid collection tank A1 to control the temperature of cultivation liquid. From the description made above, depending upon the physical requirements, the heating unit 8 may be arranged between the exit of the light permeable pipeline and the entrance of the pressure liquid infusion unit 2 to control the temperature of cultivation liquid.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An alga microbe photosynthetic reaction system, comprising:
   a photosynthetic reaction unit being a light permeable pipeline;
   a communicating unit connected to an outlet of the photosynthetic reaction unit;
   a pressure liquid infusion unit having an entrance connected to an outlet of the communicating unit;
   an injection and oxygen discharge device, wherein the injection and oxygen discharge device is a hollow pipe, and comprises an oxygen discharge can and a liquid collection can that are joined to each other, the oxygen discharge can is provided with a liquid entrance, a top exhaust, and a hollow pipe wall, and the liquid entrance leads to an exit of the pressure liquid infusion unit, the top exhaust is located at a top of the oxygen discharge can, and the hollow pipe wall extends from the top exhaust downwards, the injection and oxygen discharge device including an exhaust pipe connected to the oxygen discharge can, a middle section of the oxygen discharge can being provided with a necking portion and a side exhaust, the side exhaust being located below the necking portion, and a top end of the exhaust pipe pierces through the hollow pipe wall; and a regulation area leading to the liquid collection can and the photosynthetic reaction unit, respectively.

2. The alga microbe photosynthetic reaction system according to claim 1, wherein the photosynthetic reaction unit comprises a plurality of straight pipes and a plurality of bent pipes and the straight pipes and the bent pipes are serially connected at intervals to form an inclined spiral light permeable pipeline of double rows.

3. The alga microbe photosynthetic reaction system according to claim 1, wherein a topmost section of the photosynthetic reaction unit is provided with an auxiliary mouth.

4. The alga microbe photosynthetic reaction system according to claim 1, wherein the communicating unit is a connection tube which leads to the photosynthetic reaction unit and the pressure liquid infusion unit, or is provided with a liquid collection tank having a opening and with a flow tube, the liquid collection tank leads correspondingly to the photosynthetic reaction unit and the tube leads to the liquid collection tank and the pressure liquid infusion unit.

5. The alga microbe photosynthetic reaction system according to claim 1, wherein the pressure liquid infusion unit is a pressure liquid infusion pump.

6. The alga microbe photosynthetic reaction system according to claim 1, wherein a bottom end of the exhaust pipe is formed with an expansion portion and is correspondingly located at an inner side of the side exhaust inside the oxygen discharge can.

7. The alga microbe photosynthetic reaction system according to claim 1, wherein the regulation area is an expansion pipe or a straight pipe used to lead to the liquid collection can and the entrance of the photosynthetic reaction unit.

8. The alga microbe photosynthetic reaction system according to claim 1, wherein the system comprises a communicating device connected to a bottom of the liquid collection can and a bottom of the regulation area and provided with a switch valve component.

9. The alga microbe photosynthetic reaction system according to claim 1, further comprising a harvesting valve component connected between the exit of the communicating unit and the entrance of the pressure liquid infusion unit.

10. The alga microbe photosynthetic reaction system according to claim 1, further comprising a heating unit connected between the exit of the photosynthetic reaction unit and the entrance of the pressure liquid infusion unit.

11. The alga microbe photosynthetic reaction system according to claim 1, further comprising a sprinkling unit located above the photosynthetic reaction unit.

12. The alga microbe photosynthetic reaction system according to claim 1, further comprising at least one light complement unit located at a side of the light-permeable pipeline.

* * * * *